(12) United States Patent
Killion et al.

(10) Patent No.: US 9,566,023 B2
(45) Date of Patent: Feb. 14, 2017

(54) AUDIOMETRY EARPHONE INSERT

(71) Applicant: Etymotic Research, Inc., Elk Grove Village, IL (US)

(72) Inventors: Mead C. Killion, Elk Grove Village, IL (US); Charles J. Aldous, Bensenville, IL (US); Viorel Drambarean, Lincolnwood, IL (US); Donald Wilson, Barrington, IL (US); Jonathan K. Stewart, Bloomingdale, IL (US)

(73) Assignee: ETYMOTIC RESEARCH, INC., Elk Grove Village, IL (US)

( * ) Notice: Subject to any disclaimer, the term of this patent is extended or adjusted under 35 U.S.C. 154(b) by 191 days.

(21) Appl. No.: 14/509,688

(22) Filed: Oct. 8, 2014

(65) Prior Publication Data

US 2015/0096379 A1 Apr. 9, 2015

Related U.S. Application Data

(60) Provisional application No. 61/888,219, filed on Oct. 8, 2013.

(51) Int. Cl.
*A61B 5/12* (2006.01)
*H04R 1/10* (2006.01)

(52) U.S. Cl.
CPC ............... *A61B 5/12* (2013.01); *A61B 5/121* (2013.01); *A61B 5/123* (2013.01); *A61B 2560/0223* (2013.01); *A61B 2560/0443* (2013.01); *A61B 2562/221* (2013.01); *A61B 2562/222* (2013.01); *H04R 1/1016* (2013.01)

(58) Field of Classification Search
CPC ........... A61B 5/123; A61B 5/12; A61B 5/121; A61B 2560/0223; A61B 2560/0443; A61B 2562/222; A61B 2562/221; H04R 1/1016
USPC .......................................................... 73/585
See application file for complete search history.

(56) References Cited

U.S. PATENT DOCUMENTS

| 4,677,679 | A | * | 6/1987 | Killion | ..................... | A61B 5/12 181/130 |
| 4,763,753 | A | * | 8/1988 | Killion | ..................... | A61B 5/12 181/130 |
| 5,812,679 | A | * | 9/1998 | Killion | ................. | H04R 25/502 381/312 |

(Continued)

*Primary Examiner* — J M Saint Surin
(74) *Attorney, Agent, or Firm* — McAndrews, Held & Malloy, Ltd.

(57) ABSTRACT

The present technology relates to an earphone apparatus adapted for use in audiometry examinations. The earphone apparatus comprises a housing and a receiver having an acoustic output adapted to connect with an audio signal source. The earphone apparatus can also include a circuit board with an electrical equalization network connected to the receiver. A coupling can be connected to the acoustic output of the receiver. A sound tube can be connected to the acoustic output and extends out from the housing to an ear piece. The earphone also includes a resonance cancellation assembly comprising a damping chamber and a tubing section acoustically connecting the damping chamber to the coupling. The damping chamber can provide an acoustic compliance to the sound delivered by the receiver. The earphone can also comprise an electrical connector with a protector that is adapted to connect with a female connector delivering electrical power.

10 Claims, 9 Drawing Sheets

(56) References Cited

U.S. PATENT DOCUMENTS

| | | | | |
|---|---|---|---|---|
| 5,887,070 A * | 3/1999 | Iseberg | ............... | H04R 1/1016 181/130 |
| 6,532,296 B1 * | 3/2003 | Vaudrey | ............ | G10K 11/1788 381/371 |
| 7,298,858 B2 * | 11/2007 | Wilson | ............... | H04R 1/1016 181/130 |

* cited by examiner

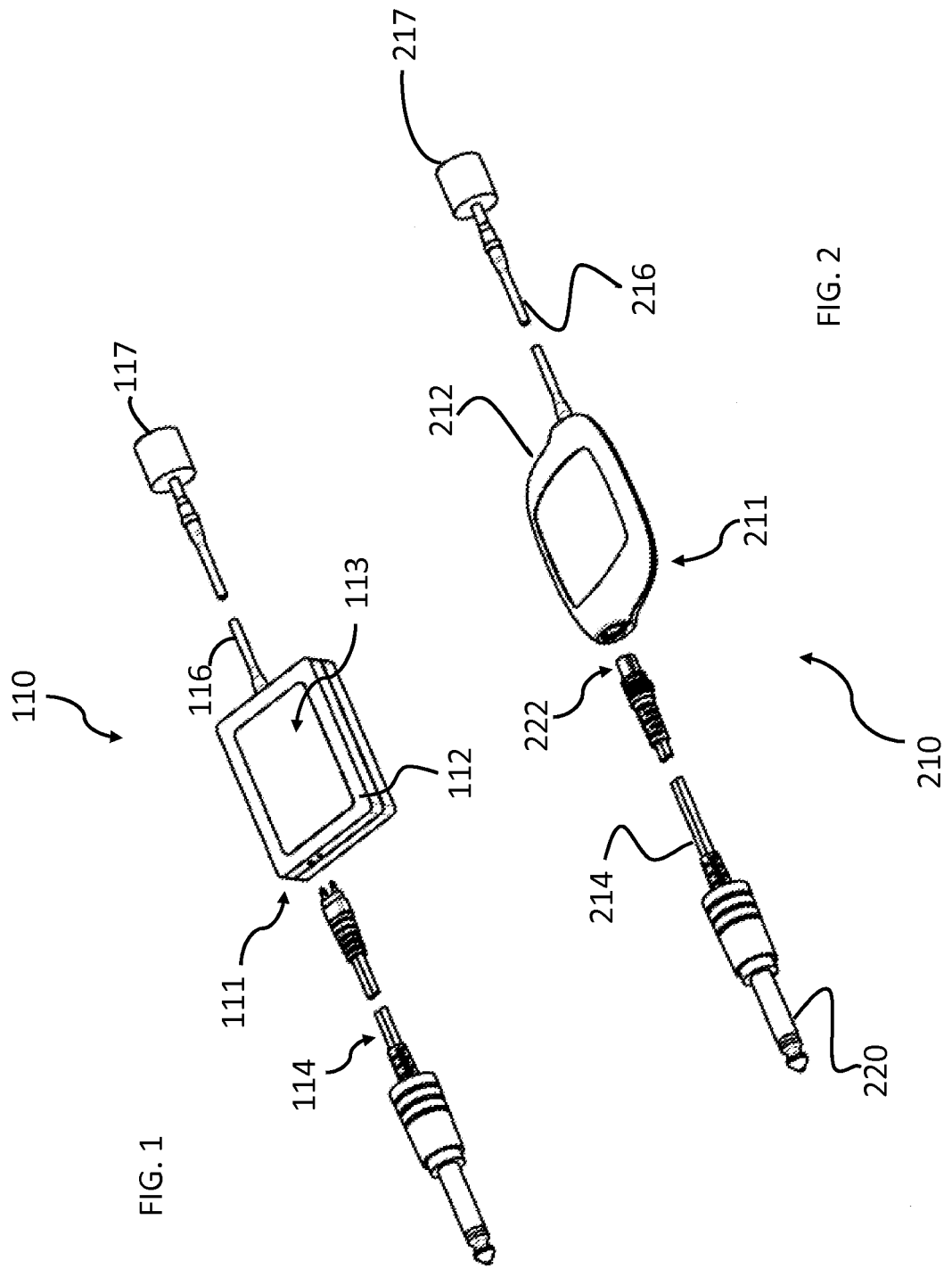

Earphone Performance measured in HA1

AUDIOMETRY EARPHONE INSERT

RELATED APPLICATIONS

The present application claims priority under 35 U.S.C. §119(e) to provisional application Ser. No. 61/888,219 filed on Oct. 8, 2013, entitled "Audiometry Earphone Insert." The above referenced provisional application is hereby incorporated herein by reference in its entirety.

BACKGROUND

Audiometry is the science of measuring hearing acuity for variations in sound. Audiometry exams test the ability to hear sounds, which can vary based on loudness (intensity) or the speed of sound wave vibrations (tone), for example. Audiometry exams can help determine a subject's hearing levels with the help of an audiometer, and can also measure a subject's ability to discriminate between different sound intensities, to recognize pitch, or to distinguish certain types of sounds (e.g., speech) from background noise. Results of audiometric exams can be used to diagnose hearing loss or diseases associated with the ear. Audiometric exams frequently involve the use of an audiometric earphone to deliver sounds to the user's ear canal.

SUMMARY

The present technology provides an earphone apparatus, for example, an earphone apparatus adapted for use in audiometry examinations. In certain embodiments, the earphone apparatus comprises a housing and a receiver located within the housing. The receiver can be adapted to connect with an audio signal source. The receiver can also comprise an acoustic output. In certain aspects, the earphone apparatus can include a circuit board comprising an electrical equalization network. The electrical equalization network can be connected to the receiver, for example. The earphone apparatus can also include a coupling that can be connected to the acoustic output of the receiver. A sound tube can be connected to the coupling and/or the acoustic output of the receiver, for example, such that the sound tube extends out from the housing, for example, to an end adapted to be inserted in the ear of a user, or a test subject. Certain embodiments of the present technology also comprise a resonance cancellation assembly. The resonance cancellation assembly can include a damping chamber and a tubing section that acoustically connects the damping chamber to the coupling. The damping chamber can provide, for example, an acoustic compliance to the sound delivered by the receiver.

In certain aspects of the present technology, the earphone can also comprise an electrical connector having at least one prong and at least one protector. The electrical connector can be adapted, for example, to connect with a female connector that is capable of delivering electrical power, for example, to the receiver of the earphone.

In certain embodiments of the present technology, the circuit board of the earphone comprises components that are adapted to operate with at least three different types of earphones, for example, an earphone that provides 10 Ohms of impedance, an earphone that provides 50 Ohms of impedance, and an earphone that provides 300 Ohms of impedance.

BRIEF DESCRIPTION OF SEVERAL VIEWS OF THE DRAWINGS

FIG. 1 shows the external appearance of an audiometry earphone in accordance with at least one embodiment of the present technology.

FIG. 2 shows the external appearance of an audiometry earphone in accordance with at least one embodiment of the present technology.

DETAILED DESCRIPTION

Figure 3:
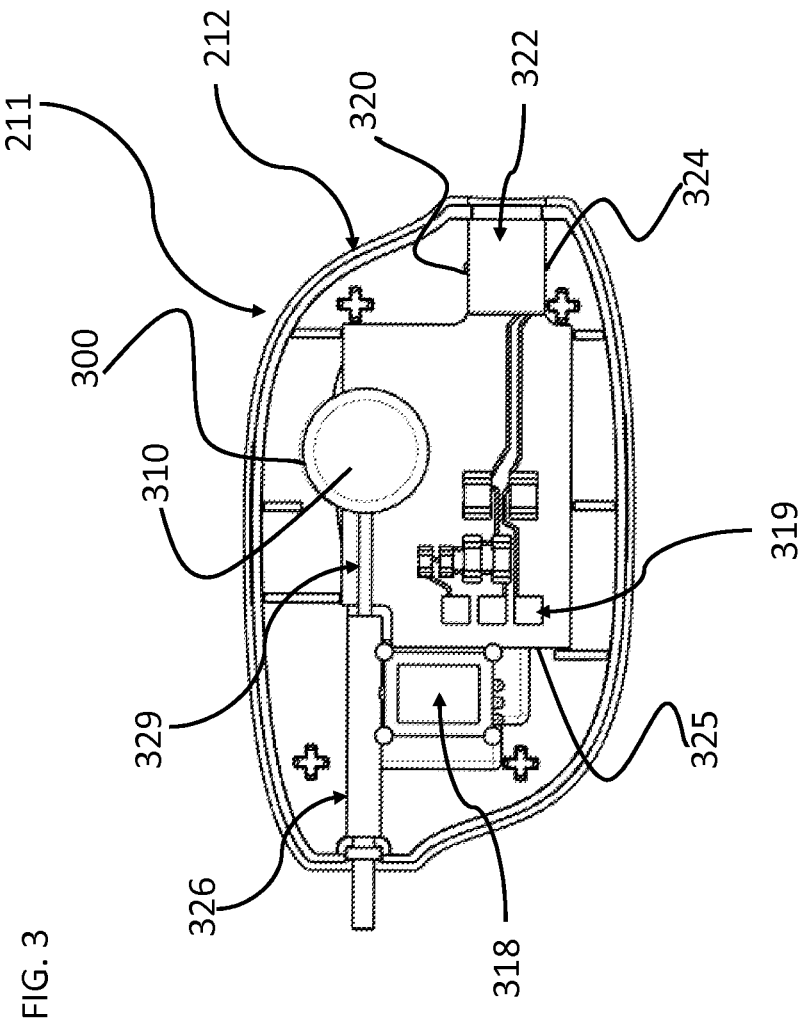
FIG. 3 shows the internal structure of an audiometry earphone base unit in accordance with at least one embodiment of the present technology.

The present technology relates to audiometric devices. More specifically, the present technology relates to systems and methods using audiometric earphones that can be used in performing audiometric examinations.

Early audiometers used headphones, for example, as the Air Force TDH-39/MX41-AR headphones, to run audiometry exams. Using headphones in audiometry exams allowed for simple calibration, and often generated reproducible results. The headphones, however, had several drawbacks with respect to the task of measuring subjects' hearing thresholds. For example, the headphones tend to generate vibrotactile signals, create a pressure on the ear, and failed to block out all outside noise. These shortcomings often result in obtaining misinformation and flawed results during audiometric exams.

Subsequently, insert earphones were developed for use with audiometers, such as those earphones described in U.S. Pat. No. 4,763,753 ("Killion"). The Killion patent is herein incorporated by reference in its entirety. The insert earphones described in the Killion patent (herein after referred to as ER-3A earphones), provided solutions to some of the shortcomings of the headphone devices. For example, the ER-3A earphones provided:

(1) improved interaural attenuation, which improves the ability of an audiometry exam to determine which of a subject's ears may require surgery or treatment;

(2) improved noise isolation provided by eartips that sealed the ear from outside noise, thereby improving the ability to perform tests in the presence of competing noise, e.g., without requiring a soundproof booth;

(3) improved accuracy in the testing of hearing impaired patients that have residual hearing for only intense low frequency sound, i.e., left corner audiograms, by increasing the accuracy of responses to auditory signals, rather than vibrotactile signals that often result from the use of headphones;

(4) reducing errors caused from ear canal collapse resulting from the pressure of the headband through the headphone ear cushions;

(5) improved correlation between hearing aid measurements and audiometric measurements;

(6) improved audiometric exam repeatability; and (7) reduction of electrical and magnetic artifacts introduced in the auditory brainstem response measurement.

Though they provide several advantages as described above, the audiometry earphones in the state of the art also have some shortcomings. For example, the ER-3A earphones have a female mating portion that is adapted to connect with a male connector that has exposed prongs. Such exposed prongs can pose safety hazards, as the prongs can carry an electrical current.

Moreover, current audiometry earphones employ a circuit board that is required for larger film capacitors, which can be expensive and bulky compared to chip capacitors, which are capable of providing 3 µF of capacitance.

Additionally, current audiometry earphones (i.e., the ER-3A earphones) use a resonance-cancelling "back tube" to provide damping. For example, the back tube design can provide a damping equivalent to that provided in the EV Carlson twin-tube (e.g., as described in U.S. Pat. No. 4,006, 321 ("Grant"), which is hereby incorporated by reference). This back tube design is formed from alternating large and small diameter tubes, providing a sausage-link appearance. Though effective, the back tube damping design can be difficult to produce to the degree of acoustic precision required, and therefore results in an increased cost of the ER-3A earphone. Moreover, the back tube design also takes up a significant amount of space within the earphone, thereby restricting the size, and location of the other equipment that can be used in the earphone. Additionally, because the back tube design involves multiple tubes and pieces of equipment, there is a higher potential that one or more of the pieces may fail, disconnect, or otherwise cause problems with the earphone.

Yet another shortcoming of the current audiometry earphones also relates to the circuit board designs. Audiometry earphones can be provided at various impedance levels, for example, audiometry earphones can be designed to provide 10 Ohms of impedance, 50 Ohms of impedance, or 300 Ohms of impedance. But due to the size and expense of the 3 µF capacitors employed by certain audiometry earphones (e.g., the 10 Ohm impedance earphones), the various earphones can require an entirely different circuit board. That is, the circuitry necessary to produce the back tube design audiometry earphone does not allow for the use of a circuit board that can be universal for all audiometry earphones of various impedance levels. Accordingly, a different circuit board could be required for 10 Ohm earphones, 50 Ohm earphones, and 300 Ohm earphones, which can make the earphones more difficult and expensive to manufacture.

The present technology describes audiometry earphones that offer advantages that can overcome these and other shortcomings of the existing audiometry earphones, while retaining many or all of the virtues of the original ER-3A earphone. Moreover, the present technology incorporates a practical miniature plug-and-socket arrangement that does not leave contacts exposed to the user's touch, thereby reducing and/or eliminating the possibility that user can be exposed to dangerous voltage levels if the earphone were connected to a relatively high voltage source (through a connected equipment potential equipment fault condition).

In the course of running experiments and generating theoretical calculations relative to the present technology, it was discovered that the back tube (i.e., "sausage-link") construction employed by the ER-3A earphone could be replaced by a simpler combination of a precision tube with a round container (i.e., a "water tub") configuration.

FIG. 1 shows the external appearance of one embodiment of an audiometry earphone apparatus 110. From the external appearance alone, the embodiment of FIG. 1 can be, for example, the earphone described in the Killion patent; however, depending on the internal structure of the earphone base unit 111, earphone apparatus 110 can depict an embodiment of the present technology. The apparatus 110 includes a base unit 111, comprising a housing 112 (or case) which is generally of a rectangular shape. The housing 112 can comprise a clip 113, which can provide a convenient way to attach the apparatus 110 to the collar of a shirt, blouse or other item of apparel that may be worn by a testing subject. The base unit 111 can be connected through a cable 114 to a signal generator or other source of audio signals; however, in certain embodiments, a signal generator can be incorporated within the base unit 111, and be energized by a battery within the base unit 111 or from an external supply voltage source.

The base unit 111 can be connected through a main sound tube 116 to an ear piece 117 which can be inserted into the end of the ear canal such that the end of the tube 116 can be positioned within the ear canal. In certain embodiments, the ear piece 117 can serve to provide an acoustical seal.

By way of example, the sound tube 116 can be a length of 278 mm (10.95 inches) of #16 tubing having an inside diameter (ID) of 1.35 mm, measured from the wall of the housing 112 to the tip of the ear piece 117. This length, in combination with a 12 mm length inside the housing, can produce an overall length of 290 mm and, taking into account the electro-acoustic delays introduced by the unit itself, and can obtain an acoustic time delay of about 1.0 milliseconds. This value can be convenient, for example, for auditory brainstem response ("ABR") time-base offset calibration. A length of this order of magnitude can also help avoid the production of undesirable electromagnetic interference from the electrical currents flowing in the base unit 111. In certain aspects of the present technology, shorter or longer lengths may be used, as would be appreciated by persons of ordinary skill in the art.

The sound tube 116 can be made from a variety of materials, for example plastic or silicone tubing. Likewise, the ear piece 117 can also be made from various materials, including, but not limited to, materials used to form slow-recovery foam plugs attached thereto.

FIG. 2 shows the external appearance of another embodiment an audiometry earphone of the present technology. The apparatus 210 includes a base unit 211 comprising a housing 212 (or case), which can have a general shape of a parallelogram with rounded corners, for example. In alternative embodiments, however, the housing 212 can have various shapes, including but not limited to a rectangle (or box), a square (or cube), an oval or egg shape, a circle or sphere shape, a triangular shape, or another shape. Like the apparatus of FIG. 1, housing 212 can comprise a clip (not shown) for attachment an article of a test subject's clothing, for example, a shirt, blouse, tie, or jacket. Base unit 211 can be connected to a signal generator or other source of audio signals via cable 214, for example. In certain embodiments, cable 214 can have a male connector 220 on one end that connects to a signal generator or audio source, and a female connector 222 on the other end that connects to a protected male connector on the base unit 211, for example. In certain embodiments, however, a signal generator (not shown) can be incorporated within the base unit 211, which can be energized, for example, by a battery within the base unit 211 or from an external supply voltage source.

The base unit 211 can be connected through a main sound tube 216 to an ear piece 217 which can be inserted into the end of the ear canal such that the end of the tube 216 can be positioned within the ear canal. In certain embodiments, the ear piece 217 can serve to provide an acoustical seal. The sound tube 216 can vary in length and dimensions. For example, in certain embodiments, the sound tube 216 can be a length of 278 mm (10.95 inches) of #16 tubing having an ID of 1.35 mm, measured from the wall of the housing 212 to the tip of the ear piece 217. In certain aspects of the present technology, shorter or longer lengths may be used, as would be appreciated by persons of ordinary skill in the art. Sound tube 216 can be made from a variety of materials, such as PVC tubing, for example. Likewise, the ear piece 217 can also be made from various materials, including, but not limited to, materials used to form slow-recovery foam plugs attached thereto.

Figure 4A:
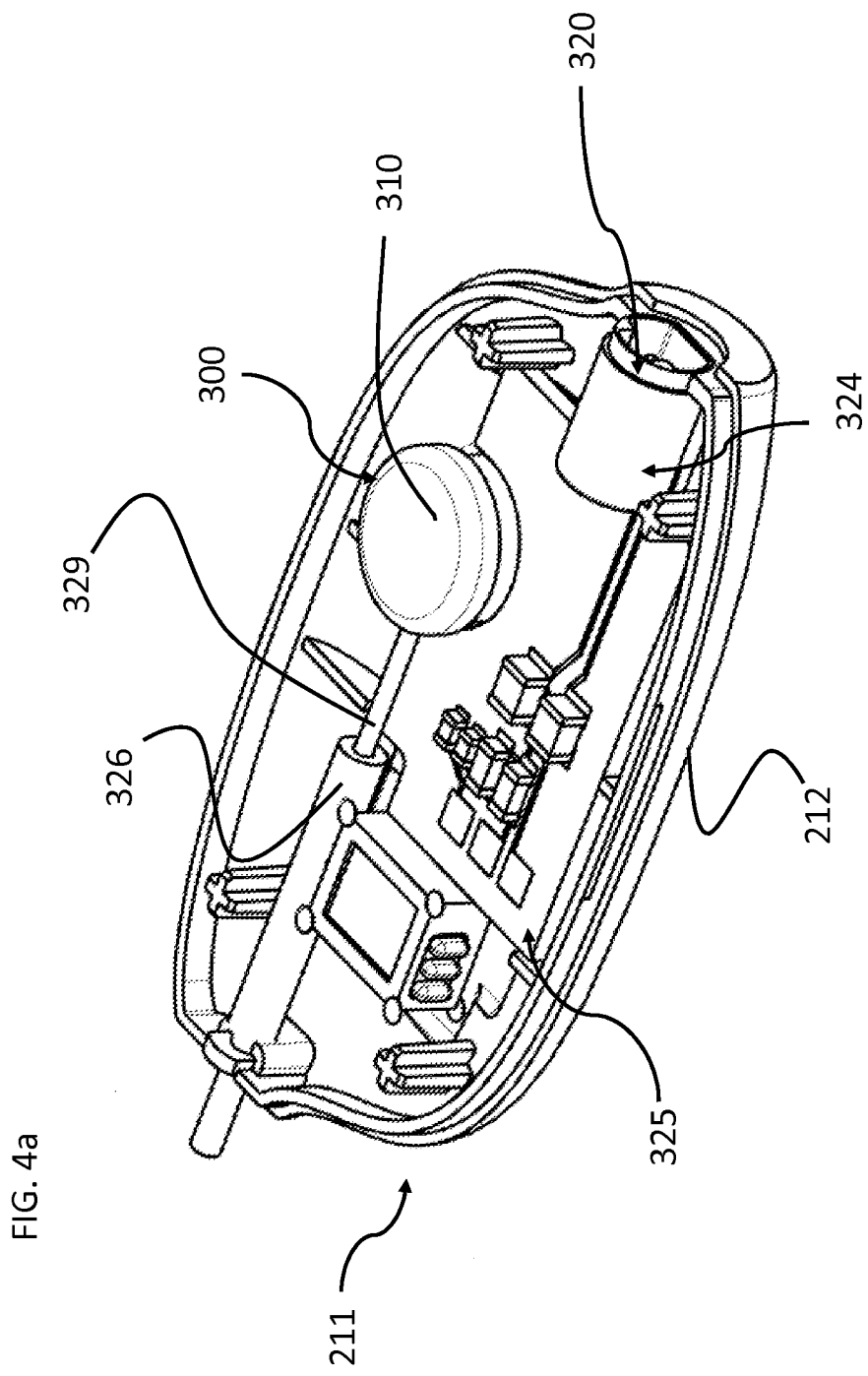
FIG. 4A shows an isometric view of an audiometry earphone base unit in accordance with at least one embodiment of the present technology.
Figure 4B:
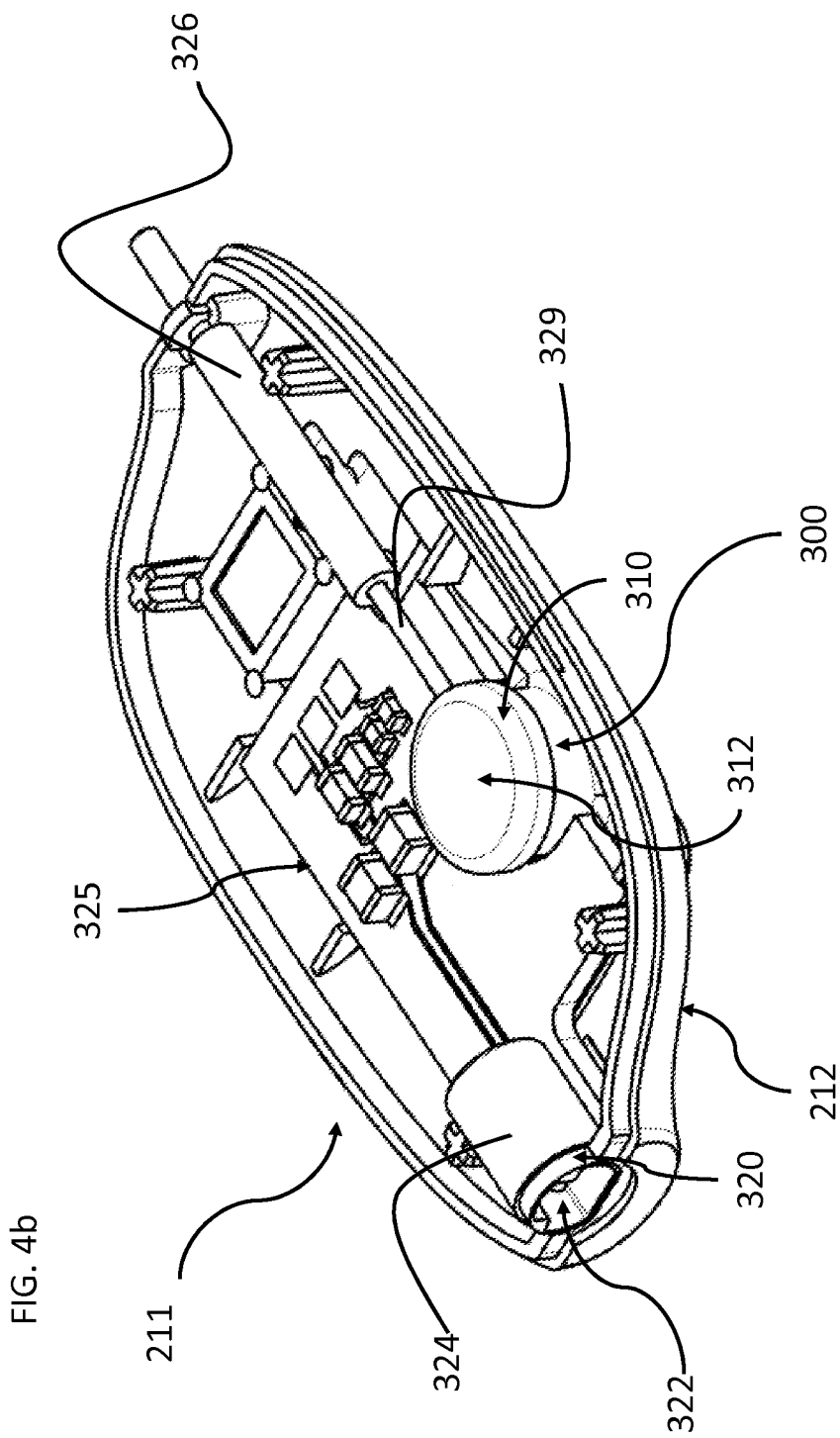
FIG. 4B shows another isometric view of the audiometry earphone base unit of FIG. 4A.

FIG. 3 shows the internal structure of a base unit of an audiometry earphone in accordance with at least one embodiment of the present technology. FIGS. 4A and 4B show isometric views of an audiometry earphone in accordance with at least one embodiment of the present technology. As shown in FIGS. 3, 4A and 4B, the base unit 211 comprises a receiver 318 which is connected to an electrical equalization network 319 integrated into a circuit board 325. In certain embodiments, the network 319 can include capacitors and resistors mounted to the circuit board 325, for example, within the base unit 211.

The acoustic output of the receiver 318 can be coupled to an intermediate point of a coupling 326, which can be of a generally tubular form, the coupling 326 being connected to the end of the sound tube (e.g., sound tube 216) through a fitting (see, e.g., FIG. 5, item 327) that can be mounted in a wall portion of the housing 212. The opposite end of the coupling 326 is connected to a resonance cancellation assembly of the present technology, generally designated by reference numeral 300.

The resonance cancellation assembly 300 includes a tubing section 329 extending from the end of the coupling 326 to a chamber 310, which can be a hollow disc or cylinder having a "water tub" appearance, for example. FIG. 4B depicts a three dimensional isometric view of the audiometric earphone 211 with a cap portion 312. The tubing section 329 defines a coupling path, the cross-sectional area of which is a fraction of the area of the main path defined by the sound tube 216 and the passage within the coupling 326. Tubing section 329 can act as an acoustic mass or inertance and it also provides an acoustic resistance. The resonance cancellation assembly 300 provides a damping chamber 310 which has a relatively large volume in relation to that provided by the tubing section 329. Accordingly, the chamber 310 acts as an acoustic compliance.

The lengths and diameters of the sections are such as to provide acoustic resistances which absorb energy at the frequencies of the undesired peaks and which smooth the overall frequency response. For example, chamber 310 can have dimensions that include a diameter of about ½", and a height of about ¼", for example, creating a volume of about 0.4 cubic inches. The chamber 310 can be comprised of various materials, for example, a plastic material or PVC. Optimum results may be obtained with use of a separate damping element 301, installed in coupling 326. In certain embodiments, the chamber 310 can take on various shapes, such as a cylinder or disc, a box or a cube, or an egg or sphere shape, for example.

At a certain frequency, the inertance of section 329 and the compliance of section 310 combine to provide a series resonance which appears in shunt relation to the flow of signal energy and effectively removes an undesirable resonance peak at that frequency. Use of the single round chamber 310 serves as a replacement over the back tube, or "sausage-like" design implemented in the ER-3A earphone.

In certain embodiments, the base unit 211 can also include an electric connector 320 that allows the earphone to receive electrical power from an external source. For example, connector 320 can be adapted to mate with a female connector (e.g., female connector 222 of FIG. 2), which can thereby be connected to a signal generator and/or an electrical power supply. The connector 320 can be arranged to include one or more prongs 322 that are protected by a protector 324 within the base unit 211. In this manner, the present technology provides an electrical connection that makes it difficult for a user to come into contact with a live electrical conductor when operating the equipment. In certain embodiments, however, a signal generator or a power source can be incorporated within the base unit 211, which can be energized, for example, by a battery within the base unit 211.

Figure 5:
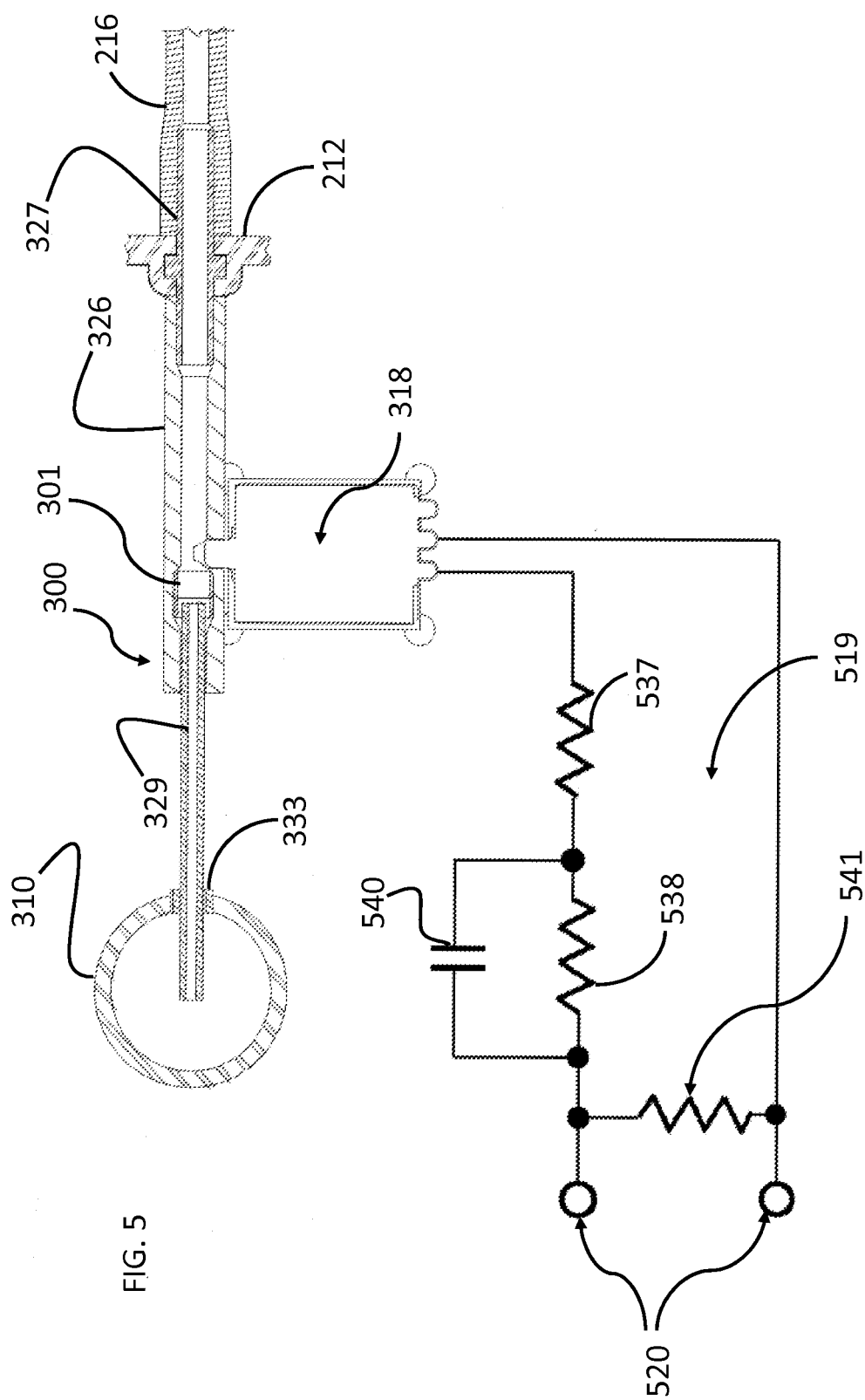
FIG. 5 shows the acoustic elements of an earphone in accordance with at least one embodiment of the present technology, in cross-section and on an enlarged scale, and also shows a schematic diagram of an electrical equalization network.

FIG. 5 shows the acoustic elements of an audiometry earphone in accordance with at least one embodiment of the present technology. More specifically, FIG. 5 depicts a cross-section of an audiometry earphone on an enlarged scale, with a schematic diagram of an electrical equalization network.

As is shown in FIG. 5, the tubing sections (e.g., 216, 326, and 329) can be provided from standard types of tubing. Sound tube 216 can be connected to the earphone housing 212 via a fitting 327. Inside the housing 212, coupling 326 is connected to a resonance cancellation assembly 300. The resonance cancellation assembly 300 includes a tubing section 329 extending from the end of the coupling 326, and connecting to the chamber 310, or "water tub." Reducer 333 can be provided between the chamber 310 and the tubing sections 329.

FIG. 5 also shows a schematic diagram of an electrical equalization network 519 which includes resistors 537 and 538 between one of the input terminals and one terminal of the receiver 318, a capacitor 540 in parallel with the resistor 538 and a resistor 541 connected across the input terminals 520. The circuit operates to enhance the high frequency response characteristics in relation to the low frequency response characteristics, such being found to be desirable for optimum results.

FIGS. 3-5 show a circuit board that can be populated with the components necessary to support audiometers of various impedance levels, including, but not limited to audiometers exhibiting impedance of 10 Ohms, 50 Ohms, and 300 Ohms, for example. The audiometry earphones in the state of the art currently require different circuit boards for the various impedance levels. That is because the 10 Ohm impedance earphone involves the use of a 3 μF capacitor, which can be large, and take up significant space on the circuit board. The present technology, however, allows for a single circuit board to be used across earphones exhibiting a wide range of impedance levels (e.g., 10 Ohms, 50 Ohms, and 300 Ohms), because the acoustic equipment takes up significantly less space within the housing 212 of the earphone. Indeed, as depicted in FIG. 4A, the present technology can incorporate a circuit board adapted to be populated with the components required for each impedance version, such that the desired impedance level can be executed by choosing the input connections. Accordingly, earphone manufacturers can stock a single circuit board in inventory, which can help reduce manufacturing and production costs.

Figure 6:
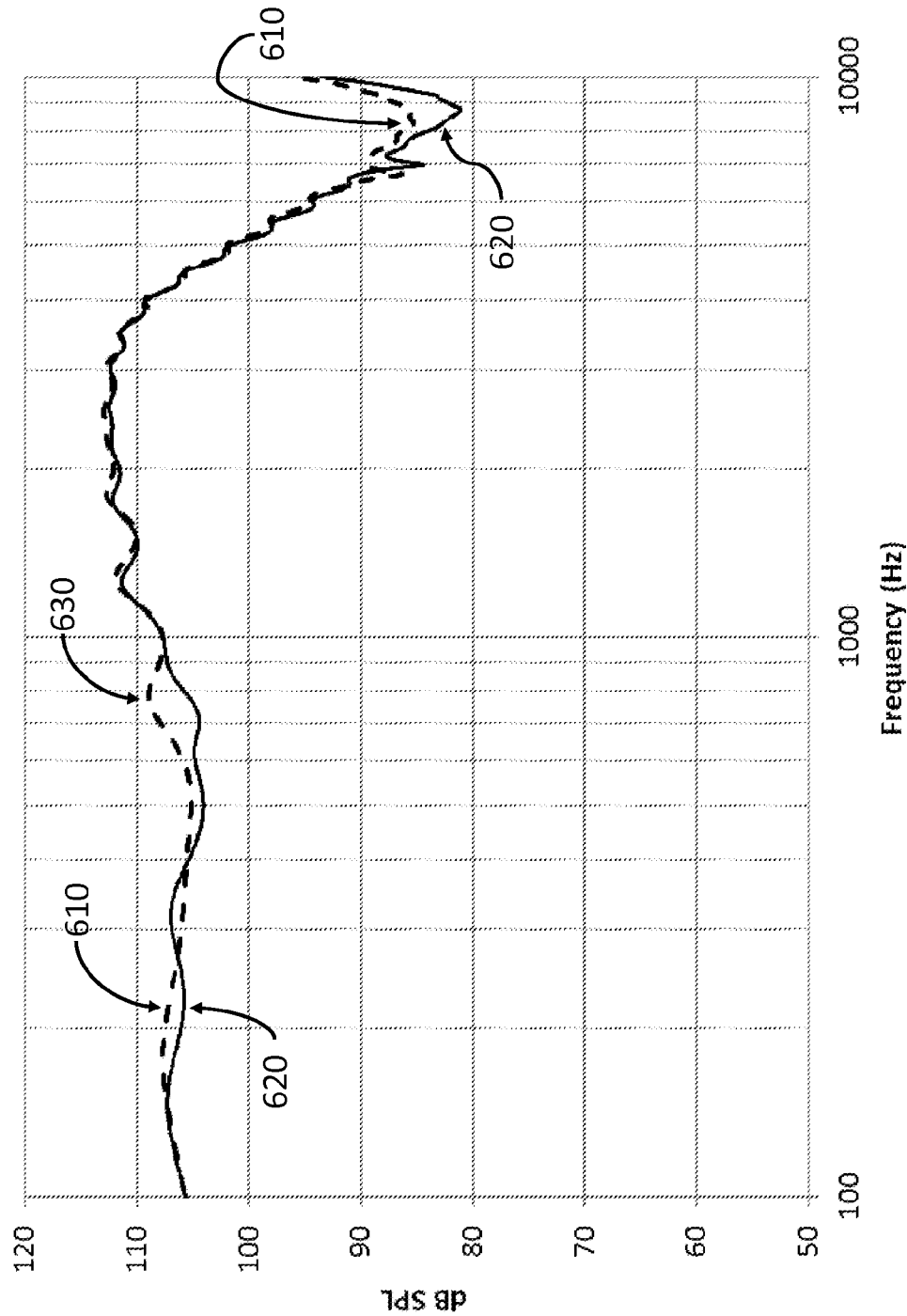
FIG. 6 shows a response comparison between an ER-3A earphone and an earphone constructed in accordance with the present technology measured in an occluded ear simulator (i.e., "Zwislocki" DB-100 coupler).
Figure 7:
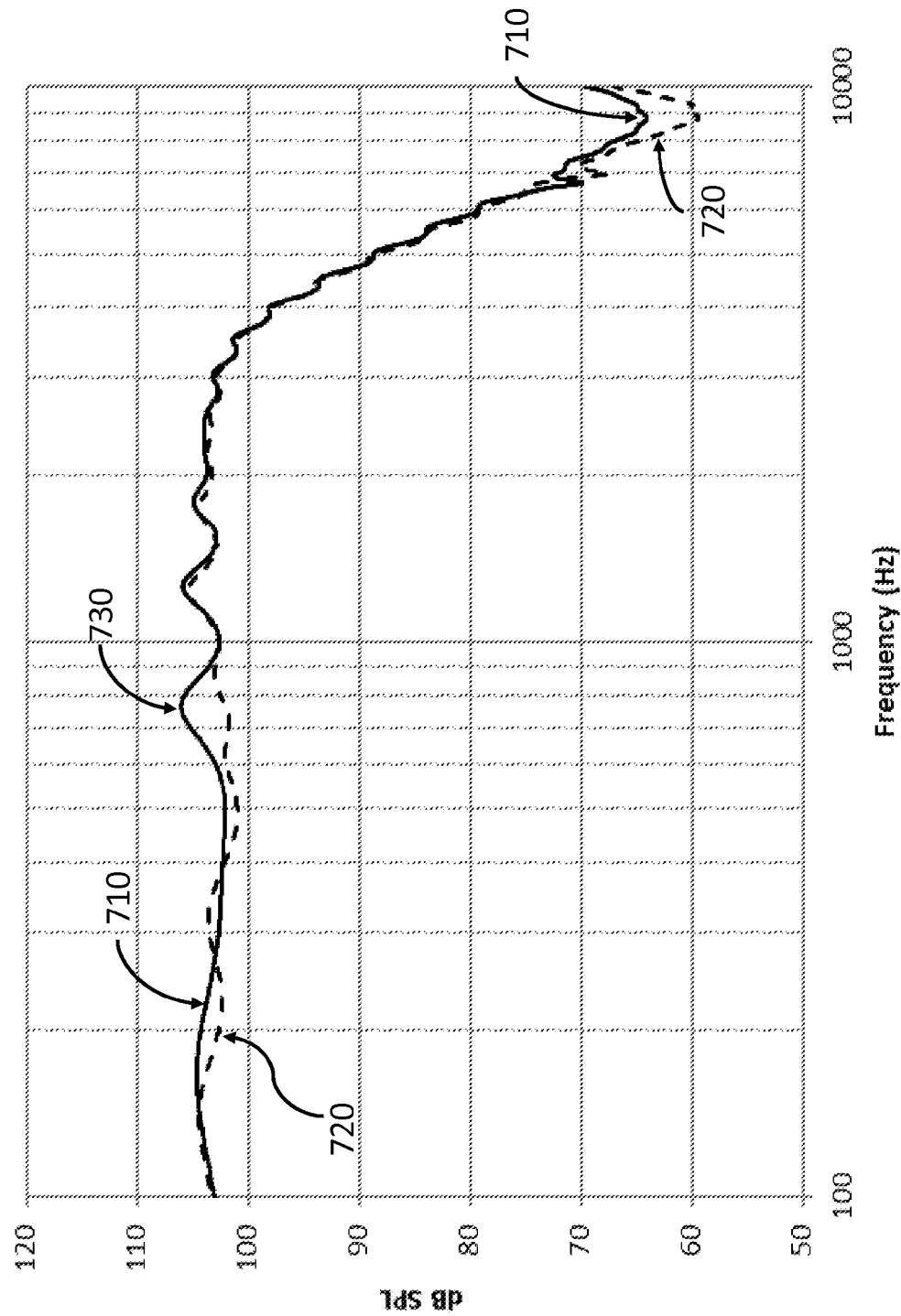
FIG. 7 shows a response comparison between an ER-3A earphone and an earphone constructed in accordance with the present technology measured in a 2 cc acoustic coupler, i.e., HA1.

As described herein, the present technology offers several advantages over other audiometric devices in the state of the art. Moreover, as depicted in the graphs provided in FIGS. 6-9, these advantages come without compromising the performance of the earphones. For example, FIG. 6 depicts the response comparison of an earphone in accordance with an embodiment of the present technology versus the ER-3A earphone measured in a DB 100, with the performance of the earphone of the present technology. Curve 610 displays the sound output level (y-axis) of the earphone of the present technology, and curve 620 displays the performance of the ER-3A earphone, measured across various sound frequency levels (x-axis). Similarly, FIG. 7 depicts the response comparison of an earphone in accordance with an embodiment of the present technology versus the ER-3A earphone, measured in HAL with the performance of the earphone of the present technology. Curve 710 displays the sound output level (y-axis) of the earphone of the present technology, and curve 720 displays the performance of the ER-3A earphone, measured across various sound frequency levels (x-axis).

As shown in FIGS. 6 and 7, the earphone of the present technology earphone can be reasonably used as a "plug and play" substitute for the ER-3A earphone, and even provides an improved performance across many frequency levels. Significantly, the earphone of the present technology displays a marked improvement over the ER-3A earphone at 750 Hz (see points 630 and 730), where the earphone of the present technology displays about 5 dB greater sensitivity.

Figure 8:
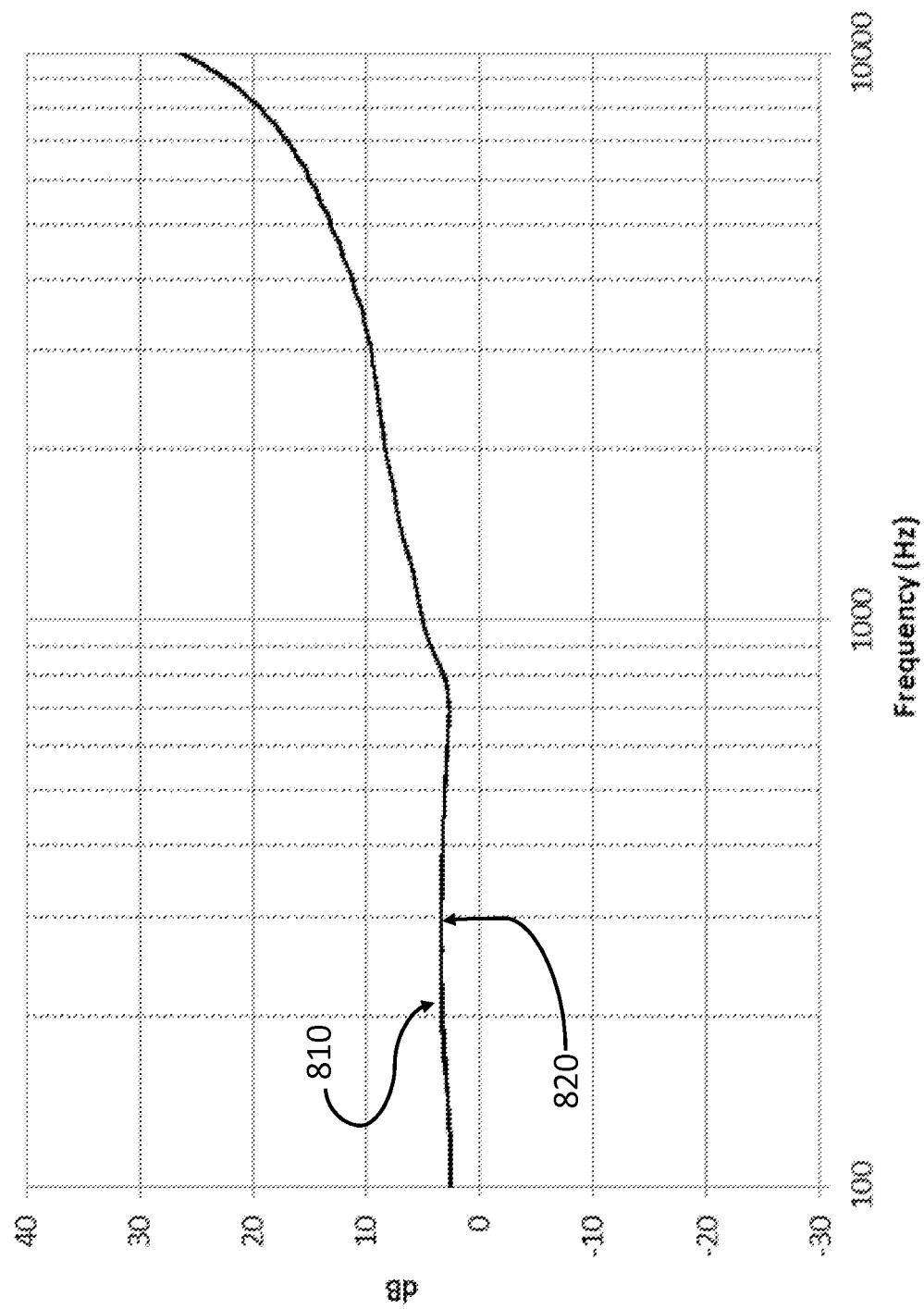
FIG. 8 shows earphone measurements taken with respect to an ER-3A earphone and an earphone constructed in accordance with the present technology measured in a DB-100 relative to a 2 cc HA1 coupler.
Figure 9:
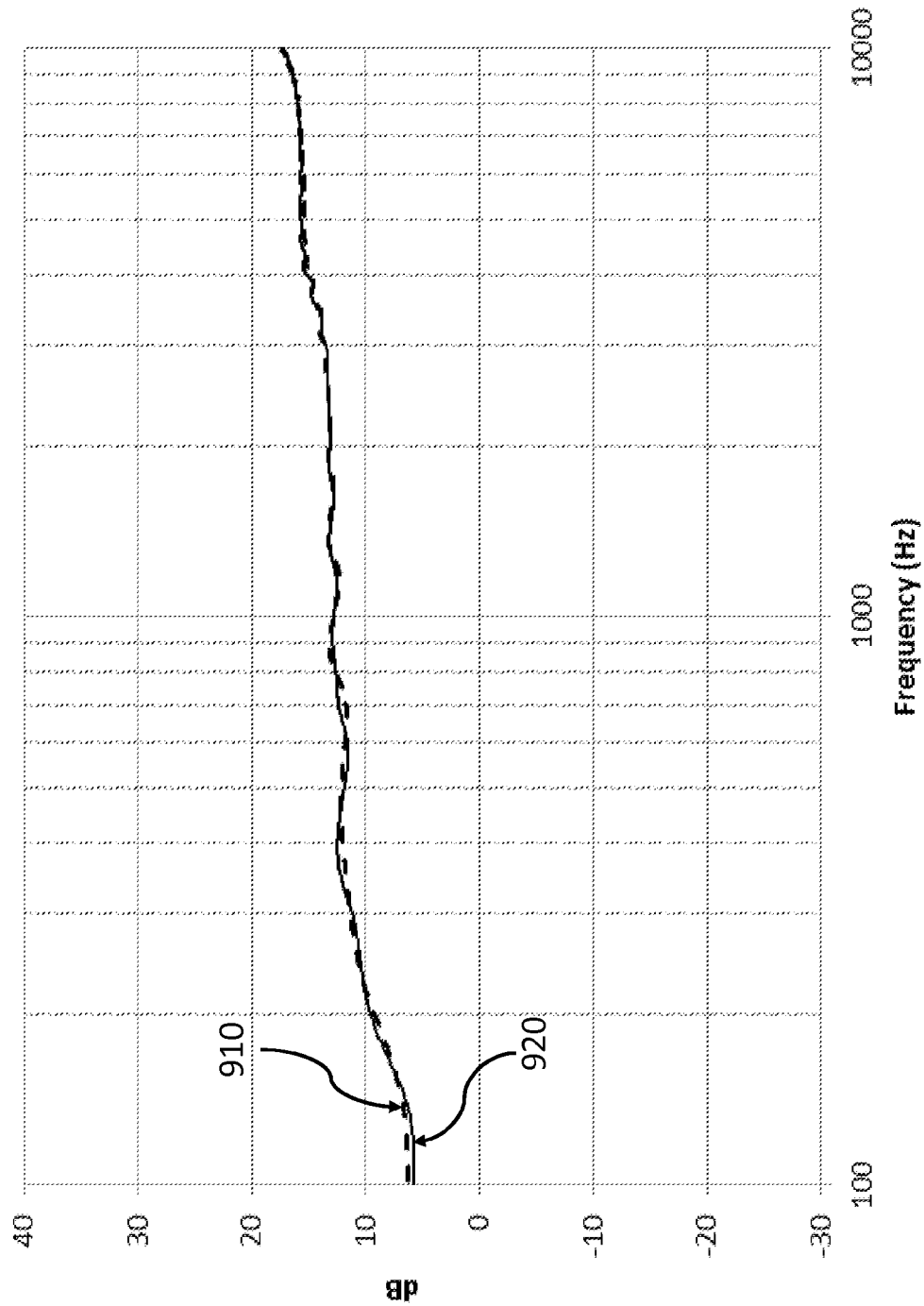
FIG. 9 shows earphone measurements taken with respect to an ER-3A earphone and an earphone constructed in accordance with the present technology measured in 0.4 cc acoustic coupler relative to a 2 cc HA1 coupler.

Generally, earphones are individually calibrated using the adjustments available in an audiometer. Accordingly, the relationship between the pressure produced in the typical HA1 2 cc coupler calibration and the pressure produced in the ear is relevant measurement to determine the quality and/or performance of an audiometry earphone. The ANSI S3.25 type DB100 "Zwislocki" occluded ear simulator or IEC 60318-4 type ear simulator provide transfer impedances similar to that of an average human ear. FIG. 8 depicts a graph charting measurements taken with respect to an ER-3A earphone and an earphone constructed in accordance with the present technology measured in Zwislocki relative to HA1. FIG. 9 shows earphone measurements taken with respect to an ER-3A earphone and an earphone constructed in accordance with the present technology measured in 0.4 cc acoustic coupler relative to HAL An advantage is that an earphone constructed in accordance with the present technology calibrated in a standard 2 cc coupler in accordance with ANSI S3.6, thereby, produces the same sound pressure level at the eardrum as the ER-3A, so calibrated. This is shown in FIG. 8, where each of the ER-3A earphone (curve 820) and the earphone of the present technology (curve 810), produce within a 1 dB or less of the same sound pressure levels in a standard occluded ear simulator. And as shown in FIG. 9, each of the ER-3A earphone (curve 920) and the earphone of the present technology (curve 910), produce within a 1 dB or less of the same sound pressure levels in a 0.4 cc acoustic coupler. Significantly, in each case, the performance of the earphones of the present technology perform the same as, or better than, the ER-3A earphones.

The present technology has now been described in such full, clear, concise and exact terms as to enable any person skilled in the art to which it pertains, to practice the same. It is to be understood that the foregoing describes preferred embodiments and examples of the present technology and that modifications may be made therein without departing from the spirit or scope of the invention as set forth in the claims. Moreover, while particular elements, embodiments and applications of the present technology have been shown and described, it will be understood, of course, that the present technology is not limited thereto since modifications can be made by those skilled in the art without departing from the scope of the present disclosure, particularly in light of the foregoing teachings and appended claims. Moreover, it is also understood that the embodiments shown in the drawings, if any, and as described above are merely for illustrative purposes and not intended to limit the scope of the invention, which is defined by the following claims as interpreted according to the principles of patent law, including the Doctrine of Equivalents. Further, all references cited herein are incorporated in their entirety.

The invention claimed is:

1. An earphone apparatus comprising:
   a housing;
   a receiver located within the housing, the receiver configured to connect with an audio signal source, the receiver further comprising an acoustic output,
   a circuit board comprising an electrical equalization network, the electrical equalization network connected to the receiver;
   a coupling connected to the acoustic output of the receiver;
   a sound tube connected to the coupling, the sound tube extending out from the housing; and
   a resonance cancellation assembly, the resonance cancellation assembly comprising a damping chamber and a tubing section acoustically connecting the damping chamber to the coupling;
   wherein the damping chamber provides an acoustic compliance.

2. The earphone apparatus of claim 1, wherein the damping chamber has a cylindrical shape.

3. The earphone apparatus of claim 1, wherein the sound tube comprises an ear piece that provides an acoustical seal within the ear of a user.

4. The earphone apparatus of claim 1, wherein the circuit board comprises components configured to operate with an earphone that provides 10 Ohms of impedance, an earphone that provides 50 Ohms of impedance, and an earphone that provides 300 Ohms of impedance.

5. The earphone apparatus of claim 1, further comprising an electrical connector.

6. The earphone apparatus of claim 5, wherein the electrical connector comprises at least one prong and at least one protector.

7. The earphone apparatus of claim 6, wherein the electrical connector is configured to connect with a female connector, wherein the female connector is configured to provide electrical power from an external source to the earphone apparatus.

8. The earphone apparatus of claim 1, wherein the earphone apparatus is configured to deliver acoustic stimuli to the eardrum of an ear.

9. An earphone apparatus comprising:
a housing;
a receiver located within the housing, the receiver configured to connect with an audio signal source, the receiver further comprising an acoustic output,
a circuit board comprising an electrical equalization network, the electrical equalization network connected to the receiver;
a coupling connected to the acoustic output of the receiver;
a sound tube connected to the acoustic output of the receiver, the sound tube extending out from the housing; and
a resonance cancellation assembly, the resonance cancellation assembly comprising a damping chamber and a tubing section acoustically connecting the damping chamber to the coupling;
an electrical connector comprising at least one prong and at least one protector, wherein the electrical connector is configured to connect to a female connector configured to deliver electrical power;
wherein the damping chamber provides an acoustic compliance.

10. An earphone apparatus comprising:
a housing;
a receiver located within the housing, the receiver configured to connect with an audio signal source, the receiver further comprising an acoustic output,
a circuit board comprising an electrical equalization network, the electrical equalization network connected to the receiver;
a coupling connected to the acoustic output of the receiver;
a sound tube connected to the acoustic output of the receiver, the sound tube extending out from the housing; and
a resonance cancellation assembly, the resonance cancellation assembly comprising a damping chamber and a tubing section acoustically connecting the damping chamber to the coupling;
an electrical connector comprising at least one prong and at least one protector, wherein the electrical connector is configured to connect to a female connector configured to deliver electrical power;
wherein the damping chamber provides an acoustic compliance, and wherein the circuit board comprises components configured to operate with an earphone that provides 10 Ohms of impedance, an earphone that provides 50 Ohms of impedance, and an earphone that provides 300 Ohms of impedance.

* * * * *